United States Patent [19]
Everaerts et al.

[11] Patent Number: 5,962,546
[45] Date of Patent: Oct. 5, 1999

[54] CATIONICALLY POLYMERIZABLE COMPOSITIONS CAPABLE OF BEING COATED BY ELECTROSTATIC ASSISTANCE

[75] Inventors: Albert I. Everaerts, Oakdale; William M. Lamanna, Stillwater; Albert E. Seaver, Woodbury; George V. D. Tiers, St. Paul, all of Minn.

[73] Assignee: 3M Innovative Properties Company, St. Paul, Mich.

[21] Appl. No.: 08/847,206

[22] Filed: May 1, 1997

Related U.S. Application Data

[63] Continuation-in-part of application No. 08/643,428, May 8, 1996, abandoned, which is a continuation-in-part of application No. 08/622,102, Mar. 26, 1996, abandoned.

[30] Foreign Application Priority Data

Jul. 9, 1996 [WO] WIPO ............... PCT/US96/11397

[51] Int. Cl.⁶ .................. C08G 59/68; C08G 77/14; H01B 1/20; B05D 1/04
[52] U.S. Cl. .............. 522/25; 522/28; 522/29; 522/31; 522/66; 522/170; 522/172; 522/167; 522/168; 522/181; 522/188; 522/184; 522/173; 522/148; 528/403; 528/405; 528/408; 528/409; 528/412; 528/417; 528/421; 528/13; 528/14; 528/25; 528/40
[58] Field of Search .................. 522/181, 31, 66, 522/78, 79, 71, 82, 173, 168, 169, 170, 25, 28, 29, 148; 528/403, 405, 408, 412, 409, 417, 421, 422, 13, 14; 252/501.1, 519.14, 519.34

[56] References Cited

U.S. PATENT DOCUMENTS

| | | | |
|---|---|---|---|
| 2,732,398 | 1/1956 | Brice et al. | 260/503 |
| 3,281,472 | 10/1966 | Heine | 260/607 |
| 3,348,965 | 10/1967 | Drum | 117/93.4 |
| 3,637,845 | 1/1972 | Moore et al. | 260/556 |
| 3,705,185 | 12/1972 | Moore et al. | 260/465 |
| 3,984,357 | 10/1976 | Koshar | 260/2 R |
| 4,053,519 | 10/1977 | Koshar | 260/607 |
| 4,059,444 | 11/1977 | Lu et al. | 96/1 |
| 4,303,924 | 12/1981 | Young, Jr. | 346/1.1 |
| 4,505,997 | 3/1985 | Armand et al. | 429/192 |
| 4,748,043 | 5/1988 | Seaver et al. | 427/30 |
| 5,072,040 | 12/1991 | Armand | 564/82 |
| 5,256,821 | 10/1993 | Armand | 564/82 |
| 5,273,840 | 12/1993 | Dominey | 429/192 |
| 5,326,598 | 7/1994 | Seaver et al. | 427/473 |
| 5,364,726 | 11/1994 | Morrison et al. | 430/115 |
| 5,393,847 | 2/1995 | Alloin et al. | 525/403 |
| 5,397,673 | 3/1995 | Watson et al. | 430/126 |
| 5,414,117 | 5/1995 | Armand et al. | 562/828 |
| 5,459,228 | 10/1995 | Armand et al. | 528/373 |
| 5,521,019 | 5/1996 | Alloin et al. | 429/33 |
| 5,530,066 | 6/1996 | Armand et al. | 525/242 |
| 5,554,664 | 9/1996 | Lamanna et al. | 522/25 |
| 5,627,292 | 5/1997 | Armand et al. | 549/555 |

FOREIGN PATENT DOCUMENTS

| | | | |
|---|---|---|---|
| 585 162 A1 | 3/1994 | European Pat. Off. | C08G 65/32 |
| 0 779 671 A2 | 12/1995 | European Pat. Off. | H01M 6/16 |
| 583259 | 1/1996 | European Pat. Off. | |
| 2 170 215 | 9/1973 | France | C09D 7/12 |
| 22 39 817 | 2/1974 | Germany . | |
| WO 93/16988 | 2/1993 | WIPO | C07C 309/83 |
| WO 94/07612 | 4/1994 | WIPO | B05D 1/04 |
| WO94/07965 | 4/1994 | WIPO . | |
| WO 95/03338 | 2/1995 | WIPO | C08F 4/00 |
| WO 96/27584 | 9/1996 | WIPO | C07C 317/04 |

OTHER PUBLICATIONS

ASTM D 5403–93.

D. D. Desmarteau, et al.: "N–Fluoro–bis (trifluoromethanesulphonyl)–imide. An improved synthesis": Journal of Fluorine Chemistry, vol. 52, No. 1, Apr. 1991, Lausanne, CH, pp. 7–12.

P. T. Flaherty, et al.: "Synthesis and evaluation of N–(phenylacetyl)trifluoromethanesulphonamides as anticonvulsant agents" Journal of Medicinal Chemistry, vol. 39, No. 7, Mar. 29, 1996, Washington, DC, US, pp. 1509–1513.

R.J. Koshar, et al.: "Bis(perfluoroalkylsulphonyl)methanes and related disulphones": Journal of Organic Chemistry, vol. 38, No. 19, Sep. 21, 1973, Washington, DC, US, pp. 3358–3363.

M. Hanack, et al.: An expedient synthesis of alkynyl trifluoromethyl sulphones: Synthesis, No. 8, Aug. 1988, Stuttgart, DE, pp. 592–595.

Chemical Abstracts, vol. 59, No. 10, Nov. 11, 1963, Columbus, Ohio, US; abstract No. 11689e, L.M. Yagupol'skii, et al.: "(Arylsulphonyl) (trifluoromethylsulphonyl) methanes" col. 11689;XP002051638 see abstract & Zh. Obshch. Khim., vol. 33, No. 3, 1963, pp. 920–928.

S.S. Magar, et al.: "Bis–alkylation of dimetallated phenylsulphonylmethyl triflone. A n+1 annulation strategy for synthesis of cyclic vinyl sulphones" Tetrahedron Letters, vol. 33, No. 6, Feb. 4, 1992, Oxford, GB, pp. 745–748.

(List continued on next page.)

*Primary Examiner*—Susan W. Berman
*Attorney, Agent, or Firm*—Lisa M. Fagan

[57] ABSTRACT

Compositions containing conductivity enhancers, which are capable of being coated onto a substrate by means of electrostatic assistance. The compositions comprise one or more cationically polymerizable monomer(s), one or more cationic initiator(s), and one or more non-volatile conductivity enhancer(s) having anionic and cationic portions which are soluble in the monomer(s) and which do not interfere with cationic polymerization wherein the anionic portion is a non-coordinating carbon-containing anion. The compositions may further comprise one or more dissociation enhancing agent(s), oligomer(s) or polymer(s), preferably co-reactive, free-radically curable monomer(s), free-radical generating initiator(s), leveling agents, and other additives or adjuvants to impart specific properties to the polymerized composition.

31 Claims, No Drawings

OTHER PUBLICATIONS

J.B. Hendrickson, et al.: "Nuclear synthons: mesyltriflone as an olefin polyanion equivalent" Journal of the American Chemical Society, vol. 108, No. 9, Apr. 30, 1986, Washington, DC, US, pp. 2358–2366.

L.M. Yagupol'skii, et al.: "Trifluorosulphonylimino and bis(trifluoromethylsulphonylimino) derivatives if arenesulphonic acids" Russian Journal of Organic Chemistry, vol. 31, No. 5, May 1995, New York, US, pp. 691–695.

D.D. Desmarteau: "Novel perfluorinated ionomers and ionenes" Journal of Fluorine Chemistry, vol. 72, No. 2, Jun. 1995, Lausanne, CH, pp. 203–208.

S.–Z. Zhu: "A new synthetic route to aryl bis(perfluoroalkanesulphonyl) methanes; structures of tolyldiazolium bis(perfluoroalkanesulphonyl)methide and 4–nitrophenylhydrazono bis(perfluoroalkanesulphonyl)methane" Journal of Fluorine Chemistry, vol. 64, No. 1–2, Sep. 1993, Lausanne, CH, pp. 47–60.

5,962,546

CATIONICALLY POLYMERIZABLE COMPOSITIONS CAPABLE OF BEING COATED BY ELECTROSTATIC ASSISTANCE

This application is a continuation-in-part of U.S. Ser. No. 08/643,428, filed May 8, 1996, now abandoned, which is a continuation-in-part of U.S. Ser. No. 08/622,102, filed Mar. 26, 1996 (now abandoned).

FIELD OF INVENTION

This invention relates to compositions capable of being coated onto a substrate by means of electrostatic assistance. More particularly, the present invention relates to cationically polymerizable compositions containing conductivity enhancers, substrates coated with these compositions, and methods for coating the substrates.

BACKGROUND OF INVENTION

The release of chemicals into the atmosphere, often polluting the air, is of substantial concern. Thus, in the chemical industry as new products and processes are developed, a key factor is the environmental effect. One means of reducing chemical emissions is to develop solvent-free processes, and to require that chemicals do not evaporate during processing or from the final product.

Liquid coatings traditionally have been solvent-based processes. Liquid coating is the process of replacing the gas, typically air, contacting a substrate, usually a solid surface such as a film or web, with a layer of liquid. After the deposition of a coating, it may remain a liquid, it may be dried if it contains solids dissolved in a volatile liquid, leaving behind a solid and typically adherent layer, or it may be "cured" (i.e., polymerized) or in some other way solidified to a functional and typically adherent layer. Volatile solvents typically have been used during coating processes and then evaporated off leaving the desired composition, especially when thin coatings are desired.

The coating process typically is selected based on the desired coat height (i.e., the coating thickness). Continuous liquid coating techniques (such as roll, curtain, slot, slide, gravure, and the like and combinations thereof) are commonly preferred for applying a composition to a smooth substrate to a height of about 5 micrometers or more. See generally, Modern Coating and Drying Technology, E. preferred for applying a composition to a smooth substrate to a height of about 5 micrometers or more. See generally, Modern Coating and Drying Technology, E. Cohen and E. Gutoff, VCH Publishing, N.Y., 1992. Rough or "three-dimensional" surfaces are preferably coated by spray processes.

Traditionally, solvent-borne thin coatings, i.e., dry thickness below about 5 micrometers, have been coated onto substrates for use as a release coating, a primer, or an anti-static layer, while thicker coatings have been used for adhesives, or for the manufacture of coated abrasives, etc. Continuous liquid coating techniques may be used to apply thin coatings; however, the composition typically has been diluted with a large amount of a solvent that is later removed by evaporation, leaving behind the composition at the desired thickness. The uniformity and thickness of the dried final layer may be difficult to control especially on rough surfaces. The added solvent leads to higher material costs, preparation costs, and solvent removal costs. In addition, the solvents typically used may be hazardous to the environment.

For continuous liquid coating processes as the line speed of the coating is increased, the process can become unstable allowing air entrapment to occur at the region where the composition first meets the substrate. This region is usually referred to as the "coating bead." Fortunately, electrostatic assistance may be used to alleviate the air entrapment problem occurring between the coating bead and the substrate. However, not all compositions can be applied by electrostatic assistance methods. The composition must have a sufficient conductivity such that free ions can move within the composition when an electric field is applied. Then as a high differential of electrical potential is applied between the composition and the substrate, an electric field is produced in the composition which induces the ions of one polarity in the composition to move to the coating bead surface which is closest to the substrate. In some coaters (e.g., gravure) which do not have a single coating bead, the ions still move to the composition's surfaces (e.g., the composition's surfaces in the gravure cells) which are closest to the substrate. This "inductive charging" of the composition causes an electrostatic pressure at the coating bead surface which can change the shape of the coating bead and prevent air from coming between the coating bead and the substrate. Thus with electrostatic assistance, increased line speeds may be obtained while maintaining uniformity when performing continuous coating. Even with discrete gravure coating methods, electrostatic assistance allows for increased line speeds because the electrostatic pressure "pulls" the composition out of the gravure cells.

Solvent-borne thin coatings may also be applied by spray processes. Although spray coating may be used to apply a composition to a smooth substrate, it is particularly useful as a method of coating rough or three-dimensional objects and sheet-like webs with rough or three-dimensional surfaces. Electrostatic spray processes are commonly preferred for applying a composition having a solvent to a rough surface to a coat height of 5 micrometers or more. However, a problem associated with spray processes is over-spraying (i.e., 50 to 80 percent of the composition may not reach the substrate). (Miller, E. P., Chapter 11, Electrostatic Coating; in Electrostatics and Its Applications, Wiley-Interscience (1973) Editor: A. D. Moore). Electrostatic spray processes provide a more controlled means of spraying, and thus reduce material loss.

In the more efficient electrostatic spray processes, the droplets are charged during formation using inductive-charging. Inductive-charging places a charge on the droplets through the electric field within the composition at the sprayer by which the electric field moves the positive free ions in opposite direction to the negative free ions. The excess of one polarity of ions accumulates at a region along the composition surface and creates the electrostatic pressure required to break the composition into a charged droplet mist. To achieve this inductive charging, the composition must have sufficient conductivity to ensure a reasonable number of free ions are present. Droplets in electrostatic spray coating typically range in diameter from about 50 micrometers ($\mu$m) to about 200 $\mu$m, whereas conventional (non-electrostatic) spray processes can have droplets as large as 500 $\mu$m.

Electrospray, a distinct sub-class within electrostatic spraying, is restricted to low flow rates, which makes it useful for applying coatings to a thickness from about 0.005 micrometers to about 10 micrometers. Electrospray may be used to apply a thin coating without a solvent. In an electrospray process, the electrostatic pressure on the composition surface at the sprayhead causes a precisely controlled formation of one or more cones of composition from which a fine filament of liquid emanates. Each filament breaks up into a mist of droplets with droplet diameters on the order of the diameter of the filament. The diameter of the droplet can be controlled by the conductivity of the coating solution. Droplet diameters are typically less than 50 µm, and can be less than 1 µm if the conductivity is sufficiently large.

Although the electrospray process is an effective means of applying a thin coating, not every composition can be electrosprayed. As is the case with all electrostatic assistance methods, the composition must meet certain processing requirements. The viscosity and conductivity requirements for the composition to be coated vary with the electrostatic assistance method and with the coating thickness desired. For electrospray, the composition must be essentially either a single phase solution or a non-ionically-stabilized dispersion or emulsion, otherwise the composition may become unstable during the electrospray process. In a single phase solution ("true solution"), each component is completely soluble.

Compositions can be electrosprayed with or without a solvent, provided the composition is either a single phase solution or a non-ionically-stabilized emulsion or dispersion. Often a solvent must also be added to the composition in order to obtain the requisite component solubility. This added solvent, particularly if organic, may present environmental problems if it evaporates during or after processing and is not captured.

When a composition is truly solvent-free, substantially all of the initial components are present in some form in the final cured product. Thin coatings exist which are solvent-cast, but do not fit this definition because the solvent evaporates off during processing. For example, although ethanol or methanol can be added to electrosprayable compositions to enhance solubility and conductivity, they evaporate during processing.

Water-based compositions, although sometimes termed "solvent-free," cannot undergo cationic polymerization, at least until thoroughly dry.

A solvent can be added to a composition to enhance conductivity. To achieve the desired conductivity range, compositions often contain a polar solvent typically considered to be a volatile organic compound ("VOC"), in addition to a conductivity enhancer, i.e., salt. These volatile organic compounds can be hazardous to the environment.

Quaternary ammonium salts have been added to printing inks to enhance conductivity. However, depending on the choice of anion, these salts may not be compatible with cationic polymerization. U.S. Pat. No. 4,059,444 discloses adding quaternary ammonium salts, having anions with relatively low molecular weights such as sulfate, borate, and iodide, to ink. These conductivity control agents are added at levels of 0.05 to about 1 weight percent to increase the conductivity of electrostatically applied inks.

U.S. Pat. No. 4,303,924 discloses adding an oil-soluble salt, such as the mineral acid and organic acid quaternary salts of the Group Va elements, to a curable printing ink containing 0 to 30% of a polar organic solvent. All examples include a polar organic solvent.

To electrospray a thin layer having uniform thickness, each droplet from the electrospray mist must have a sufficiently low viscosity to allow for reasonable spreading on the substrate. However, for some applications it may be desirable to cure individual droplets on the substrate, e.g., slip sheets. Solvents and reactive diluents have been added to control viscosity. For example EPO Appln No. 93.924905.8 (Leir et al.) discloses adding reactive diluents to adjust viscosity for a cationically co-polymerizable polysiloxane release coating capable of being electrosprayed.

Regardless of the method of applying a coating to a substrate, the components preferably do not detrimentally interfere with the final performance of the product. A component preferably evaporates or does not interfere with polymerization or becomes physically trapped in the coating during processing, otherwise the component may migrate into the substrate and detrimentally affect the product's performance. Alternatively, it may later evaporate polluting the environment, or may later contact another surface, rub off, and contaminate that surface. To utilize the advantages electrostatic assistance methods offer, the compositions must have sufficient conductivity. Thus, the need exists for coating compositions capable of being applied by electrostatic assistance (i.e., electrostatically assisted continuous liquid coating (roll, curtain, slot, slide, gravure, and the like), electrostatic spray coating, or electrospray coating) where substantially all of the components are present in the final product and either co-polymerize with the other components or otherwise become a permanent part of the coating.

SUMMARY OF THE INVENTION

We have found compositions that are capable of being applied to a substrate by means of electrostatic assistance, the components of which do not interfere with polymerization, and when placed upon a substrate and substantially polymerized, the compositions do not undesirably degrade the properties of the product.

By incorporating conductivity enhancers in accordance with the invention, a composition which was insufficiently conductive for coating via electrostatic assistance may be formulated to achieve the desired conductivity. In addition to achieving adequate conductivity, the conductivity enhancers must be soluble in the composition, not adversely affect the composition's viscosity, preferably either substantially co-polymerize or become a permanent part of the final composition, and not undesirably degrade the final product. Non-volatile salts having noncoordinating carbon-containing anions satisfy these requirements.

The present invention provides compositions containing conductivity enhancers which are capable of being coated onto a substrate by means of electrostatic assistance. The compositions comprise one or more cationically polymerizable monomer(s), one or more cationic initiator(s), and one or more non-volatile conductivity enhancer(s) having anionic and cationic portions which are soluble in the monomer(s) and which do not interfere with cationic polymerization, wherein said anionic portion is a non-coordinating organophilic carbon-containing anion. The monomer(s) and initiator(s) are such that when in combination they have a conductivity insufficient to be applied to a substrate by means of electrostatic assistance. The compositions may further comprise one or more dissociation enhancing agent(s), free-radically curable monomer(s), free-radical generating initiator(s), leveling agents, oligomer(s) or polymer(s), preferably co-reactive, as well as other additives and adjuvants to impart specific properties to the polymerized coating. The viscosity requirements vary with the electrostatic assistance coating method.

Another embodiment of the present invention is a "solvent-free" composition which can be applied to a substrate by electrostatic assistance.

Another embodiment of the present invention is a composition which can be electrosprayed onto a substrate, and in particular a rough or a three-dimensional substrate.

DETAILED DESCRIPTION

The addition of certain types of salts as conductivity enhancers to an organic composition comprising cationically polymerizable monomers significantly enhances the composition's conductivity without the addition of a solvent. The addition of a conductivity enhancer allows compositions having insufficient conductivity for application by electrostatic assistance to achieve the requisite conductivity and thus be electrostatically coatable by continuous liquid coating, electrostatic spray coating, or electrospray coating procedures.

The conductivity requirement applies only to the application process. Once the composition is applied to a substrate, the conductivity can be significantly reduced or eliminated.

Electrostatic assistance coating methods which rely on inductive charging require free ions (i.e., ions which are physically separated such that they behave as noncoordinated ions) in solution to serve as ionic conductors. Known ionic conductors include salts, acids, water, and polar solvents containing dissociated species. Water is not compatible with cationic polymerization. Acids are often volatile and corrosive. As discussed above, polar solvents may be used to enhance the conductivity by acting as a dissociation enhancing agent. However, polar solvents often evaporate during processing and thus can be harmful to the environment. Therefore, to create a solvent-free composition which can be applied by electrostatic assistance methods, salts are useful to enhance conductivity. However, not all salts are useful in organic compositions.

A single definition is not universally used for a solvent-free composition or a high-solids solution. Ideally, a solvent-free composition is 100% reactive and does not have or produce any VOCs. As known in the art, this ideal composition is difficult if not impossible to achieve. In particular, bulk polymerization significantly slows down at higher conversions, and thus 100 percent conversion or polymerization is difficult to achieve, even without considering economic limitations. To account for the non-ideal nature of compositions, some level of non-reactive components or volatile components is presumed. The U.S. Environmental Protection Agency (EPA) established a test methodology for measuring the VOC content for radiation curable materials, as found in American Society for Testing and Materials (ASTM) standard D 5403-93. Test Method A is applicable to "radiation curable materials that are essentially 100% reactive but may contain traces (no more than 3%) of volatile materials as impurities or introduced by the inclusion of various additives". To determine the presence of volatile materials, the composition is cured and then is heated to $100\pm5°$ C. for 60 minutes in a forced draft oven. Weight measurements are taken (all at room temperature) of the substrate, the composition prior to cure, the composition after cure and the cured composition after heating. In the present invention, "solvent-free" compositions are those that comply with this standard and thus have a VOC content of no more than 3 weight percent.

In addition to meeting this standard, the solvent-free compositions of the present invention are preferably such that less than 2 weight percent of the total of all original components are heat-extractable during the application of ASTM D 5403-93, Test Method A. Thus, preferably at least 98 weight percent of the monomer(s), initiator(s), conductivity enhancer(s), and other additives are present in the final polymerized product regardless of the energy source used for the free-radical cure. The non-ideal nature of the polymerization is also allowed for in the less than 2 weight percent loss requirement.

To achieve this solvent-free composition, each component must be selected such that during processing, polymerization, and in the final product, the composition does not lose material by evaporation or "heat-extraction" to the extent of 2 weight percent or more.

In addition, the components preferably do not migrate into other layers of the final product, otherwise the product's properties may be detrimentally altered.

The conductivity requirements for the composition vary with the electrostatic coating method (see Table A) and the coating method may be determined by the desired coat height.

Walden's Rule (Jordan, P. C., *Chemical Kinetics and Transport*, Plenum Press, New York (1980)) provides that for a given system the product of the ionic conductivity times the viscosity is approximately a constant. Thus, ionic conductivity can be increased by decreasing viscosity. However, in spray coatings the droplet viscosity preferably is held quite low to allow for reasonable spreading and smoothing of the coating in a short time. Consequently, in electrostatic coating, and in particular in electrospray coating, the composition's viscosity is typically less than 1 pascal-second. Similar restrictions apply to the other methods. (See Table A.) Because the viscosity is already required to be low for most electrostatic assistance methods, the desired conductivity cannot readily be obtained by adjusting the viscosity.

TABLE A

| Method | Range | | Preferred Range | | Most Preferred Range | |
|---|---|---|---|---|---|---|
| | Viscosity $\eta$ (mPa · s) | Conductivity $\sigma$ (S/m) | Viscosity $\eta$ (mPa · s) | Conductivity $\sigma$ (S/m) | Viscosity $\eta$ (mPa · s) | Conductivity $\sigma$ (S/m) |
| Electrospray | 1 to 1000 | $10^{-7}$ to $10^{-1}$ | 1 to 100 | $10^{-6}$ to $10^{-3}$ | 1 to 50 | $10^{-5}$ to $10^{-4}$ |
| Electrostatic Spraying | 1 to 2000 | $10^{-7}$ to $10^{-1}$ | 1 to 500 | $10^{-5}$ to $10^{-1}$ | 1 to 250 | $10^{-5}$ to $10^{-1}$ |
| Continuous Liquid with Electrostatic Assist | 1 to 10,000 | $10^{-7}$ to $10^{-1}$ | 1 to 1000 | $10^{-7}$ to $10^{-1}$ | 1 to 500 | $10^{-7}$ to $10^{-1}$ |

Without the requisite conductivity, a composition cannot be applied by electrostatic assistance. This substantially limits the use of these application methods. However, by adding certain types of salts to these compositions to provide sufficient conductivity in accordance with the present invention, previously non-electrostatically-assistable compositions may now be applied to substrates by electrostatic assistance methods.

Conductivity Enhancers

Salts, as conductivity enhancers, contain ions held together by coulombic attraction. Simply having ions present does not mean that a salt solution is a sufficient ionic conductor. Electrostatic attraction binds oppositely charged ions together into ion pairs substantially reducing ionic conductivity. Therefore, to be sufficient conductors the ion pairs must at least partially dissociate and the ions become independent, i.e., become free ions (or, less preferably, ion triplets). Free ions can significantly increase the ionic conductivity of a composition provided they have enough inherent mobility to respond readily to the electrical field applied to the composition. The ability of the ion pairs to dissociate in a composition depends on several factors such as the dielectric constant of the medium.

As with other additives, the ion pairs (i.e., the salt) must be soluble to form a true solution for the composition to be potentially electrosprayable. Ions are required for various monomer mixtures to become conductive, but the solubilities of the salts differ, making some salts more effective than others. Because the compositions of interest are organic, salts with at least one organic ion typically have better solubilities. The solubility of such an organic salt can be tailored by proper selection of the organic group.

Generally, materials with higher dielectric constants (higher polarity) are better able to stabilize free ions. Polar materials reduce the attraction between oppositely charged ions, allowing the ion pairs to separate into free ions. In general, dissolved salt ions may be tightly paired (coordinated), and thus essentially non-conductive, or may be (as a result of their structure and environment) readily physically separated such that the ions behave as noncoordinated (or free) ions which are substantially conductive. As organic compositions become less polar and thus have a lower dielectric constant, the equilibrium between the free ions and the tight ion pairs shifts toward the latter. Therefore, salts dissolving to form ion pairs which readily dissociate into free ions despite less favorable conditions (i.e., low polarity and low dielectric constant mixtures) are desirably selected to enhance conductivity.

It is believed that the ease of dissociative separation of two ions is favorably influenced by charge delocalization in one or both of the ions and/or by steric hindrance around the charge center which prevents the counter-ion from tightly coordinating into an ion pair. Steric hindrance around the charge site of the ion can diminish accessibility to the counter-ion and therefore ions tend to be paired less tightly. If sterically hindering groups do not interfere with salt solubility, greater steric hindrance will favor ion-pair separation into individual ions and tend to enhance the composition's ionic conductivity. However, increased ionic size will eventually reduce conductivity due to reduction in ion mobility. Electron withdrawing groups, particularly fluorine or fluorinated groups, generally increase charge delocalization within the anionic portion and thereby enhance conductivity.

Ions can have multiple charges. Generally, monovalent ions more readily solubilize and dissociate into free ions with the selected monomer mixtures. Bivalent and trivalent ions may also be used, but unless well "stabilized" are generally less preferred because the extra charge favors tight ion aggregation over larger distances. Polymeric ions, such as from a salt of polyacrylic acid, are by their size severely restricted in mobility, and thus, limited in conductivity especially in viscous media.

The conductivity enhancers are non-volatile, or their vapor pressures are 1 kPa or less at 25° C., preferably 0.5 kPa or less at 25° C., and more preferably 0.1 kPa or less at 25° C. Preferably, the conductivity enhancers do not decompose to form volatiles, or become heat or water extractable at any time during processing, or from the final product. Preferably, the conductivity enhancers increase the composition's conductivity when added in relatively low amounts. Typically, from about 0.001 weight percent to about 10 weight percent is added, preferably from about 0.001 weight percent to about 1 weight percent is added. Further, the conductivity enhancers must not interfere with polymerization. Conductivity enhancers useful in the present invention include salts having an inorganic or organic cation and a bulky, carbon-containing, non-coordinating organophilic anion to promote dissolution and ionic dissociation of the salt in organic monomers. Preferably the anion has a formula weight of at least 200 kg/kmol.

Preferably, at least one part of the selected conductivity enhancer copolymerizes with the rest of the composition. However, if the conductivity enhancers are added in a small quantity and are physically trapped within the cured composition and thus substantially do not migrate to other layers of the substrate, evaporate, or become extractable when heated or exposed to water, the conductivity enhancers need not copolymerize. Migrating conductivity enhancers may undesirably interfere with the final product's properties.

Useful anions include, but are not restricted to, alkyl, cycloalkyl, and aryl sulfonates, fluoroalkylsulfonylimides, fluoroalkylsulfonylmethides, arylborates, carborane anions, and metallocarborane anions. In certain cases boron catecholates are useful. Preferably the anions are halogen-substituted and most preferably the halogen is fluorine.

The most preferred salts (conductivity enhancers) of this invention comprise fluorinated anions which are (fluoroalkylsulfonyl)imide (I), (fluoroalkylsulfonyl)methide (II), fluoroalkylsulfonate (III), or fluorinated or fluoroalkylated arylborate anions (IV) having the respective formulae:

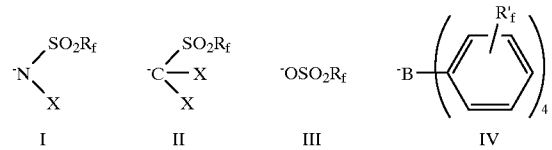

where X is selected from the groups: H, alkyl, alkenyl, aryl, alkaryl, —SO$_2$R, —SO$_2$R$_f$, —C(O)R, —SO$_2$F, and —C(O) R$_f$, but is preferably —SO$_2$R$_f$.

R is selected from the group consisting of alkyl, cycloalkyl, aralkyl, substituted alkyl, aryl, and substituted aryl groups. The substituted aryl may contain halogen or haloalkyl substituents, preferably fluorine or fluoroalkyl substituents.

R$_f$ can be a monovalent fluorinated saturated aliphatic radical containing at least one carbon atom. Where the radical contains a plurality of carbon atoms in a skeletal chain, such chain may be branched or cyclic. The skeletal chain of carbon atoms can be interrupted by heteromoieties, such as divalent oxygen or trivalent nitrogen atoms each of which is bonded only to carbon atoms, or hexavalent sulfur atoms, each of which may be bonded to carbon, fluorine, or oxygen atoms, but preferably where such heteromoieties are present, such skeletal chain does not contain more than one said heteromoiety for every two carbon atoms. An occasional carbon bonded hydrogen atom, bromine atom or chlorine atom may be present. Where present, however, they preferably are present not more than once for every two carbon atoms on the average. Thus, the non-skeletal valence bonds are preferably carbon-to-fluorine bonds. That is, $R_f$ is preferably perfluorinated.

The total number of carbon atoms in $R_f$ can vary and be, for example, 1 to 12, preferably 1 to 8, more preferably 1 to 4. Where $R_f$ is or contains a cyclic structure, such structure preferably has 5 or 6 ring members, one or two of which can be said heteromoieties, e.g., oxygen and/or nitrogen. Where two or more $R_f$ groups occur in a single formula, they can be the same or different and may be linked together to form a cycle. Alternatively, $R_f$ can be a fluorinated or fluoroalkylated aromatic group or a fluorine atom.

The $R_f'$ moiety in formula (IV) represents one or more fluorinated substituent(s) per aromatic ring and can be one or more fluorine atoms or $R_f$ groups according to the above description wherein $R_f$ is preferably $CF_3$. Preferably, the total number of non-ring carbon atoms per aromatic ring represented collectively by $R_f'$ is not greater than 4. Most preferably formula (IV) is PFTPB (tetrakis [pentafluorophenyl]borate) and TFPB (tetrakis[3,5-bis-trifluoromethylphenyl]borate). A plurality of $R_f'$ moieties associated with a single borate anion may be the same or different and may be arranged in any combination.

R and $R_f$ may further contain polymerizable functionality which is reactive with the monomers in which the salt is dissolved, thus providing a mechanism for immobilization of the anion during polymerization. Such immobilization may be necessary in applications where the extraction, leaching, or migration of the salt in the cured composition is undesirable.

Of the anions represented by formulae (I) through (IV), the imide, methide, and arylborate anions of formulae (I), (II), and (IV) are most preferred based upon solubility and conductivity.

Examples of anions useful in the practice of the present invention include, but are not limited to:

$(C_2F_5SO_2)_2N^-$,
$(C_4F_9SO_2)_2N^-$,
$(C_8F_{17}SO_2)_3C^-$,
$(CF_3SO_2)_3C^-$,
$(CF_3SO_2)_2N^-$,
$(C_4F_9SO_2)_3C^-$,
$(CF_3SO_2)_2(C_4F_9SO_2)C^-$,
$(CF_3SO_2)(C_4F_9SO_2)N^-$,
$[(CF_3)_2NC_2F_4SO_2]_2N^-$,
$(CF_3)_2NC_2F_4SO_2C^-(SO_2CF_3)_2$,
$(3,5-(CF_3)_2C_6H_3)SO_2N^-SO_2CF_3$,
$(CF_3SO_2)(FSO_2)N^-$,
$(CF_3SO_2)_2(FSO_2)C^-$,
$(CF_3SO_2)_2(H)C^-$,
$(CF_3SO_2)_2(C_6H_5)C^-$,

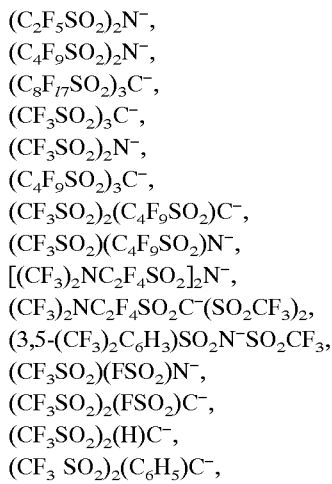

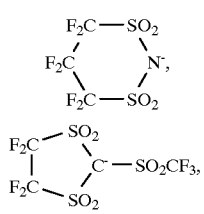

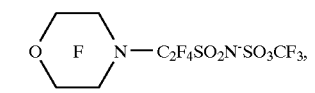

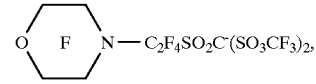

$C_6F_5SO_2C^-(SO_2CF_3)_2$,
$C_6F_5SO_2N^-SO_2CF_3$,

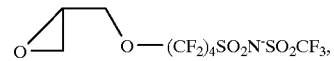

$(F-C_6H_4SO_2)(CF_3SO_2)N^-$,
$(H-CF_2CF_2SO_2)N^-$,
$(ClCF_2CF_2SO_2)_2N^-$,

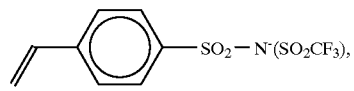

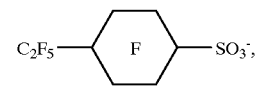

$CF_3SO_3^-$,
$(CF_3)_2NC_2F_4SO_3^-$,
$C_4F_9SO_3^-$,
$3,5-(CF_3)_2C_6H_3SO_3^-$,

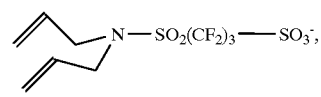

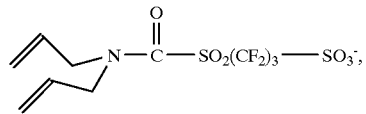

$[3,5-(CF_3)_2C_6H_3]_4B^-$,
$(C_6F_5)_4B^-$,
$(C_6H_4-p-CF_3)_4B^-$,
$(C_6H_4-m-CF_3)_4B^-$,
$(C_6H_4-p-F)_4B^-$,
$(C_6F_5)_3(CH_3)B^-$,
$(C_6F_5)_3(n-C_4H_9)B^-$,
$(C_6H_4-p-CH_3)_3(C_6F_5)B^-$,
$(C_{65})_3FB^-$,
$(C_6H_5)_3(C_6F_5)B^-$,
$(CH_3)_2(C_6H_4-p-CF_3)_2B^-$, $(C_6F_5)_3(n\text{-}C_{18}H_{37}O)B^-$,

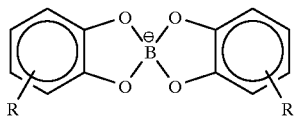

In general, the above-described bis (perfluoroalkylsulfonyl)imide and cyclic perfluoroalkylenedisulfonylimide salts can be prepared as described in U.S. Ser. No. 08/531,598 (Lamanna et al.) and U.S. Ser. No. 08/398,859 (Waddell) incorporated herein by reference in their entirety. These salts are prepared from the reaction of fluoroalkylsulfonyl fluorides, $R_fSO_2F$, or perfluoroalkylenedisulfonyl fluoride, $FSO_2R_{f3}SO_2F$, with anhydrous ammonia. Symmetrical imides in which $R_{f1}$ and $R_{f2}$ are the same can be prepared in a single step using a weakly basic organic solvent such as triethylamine as shown in Scheme I, whereas unsymmetrical imides in which $R_{f1}$ and $R_{f2}$ are different must be prepared in two steps as shown in Scheme II.

Scheme I

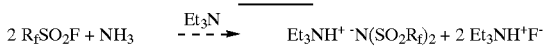

Scheme II

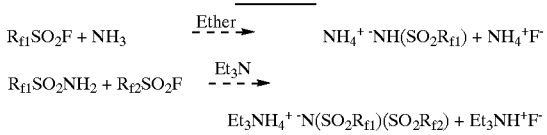

Cyclic perfluoroalkylenedisulfonylimide salts can be prepared as described in U.S. Pat. No. 4,387,222, incorporated herein by reference in its entirety.

Perfluoroalkylsulfonylfluorides and perfluoroalkylenedisulfonyl-fluorides used as precursors to the imide and methide salts of this invention can be prepared by a variety of methods known in the art as described, for example, in U.S. Pat. Nos. 3,542,864; 5,318,674; 3,423,299; 3,951,762; 3,623,963; 2,732,398, and S. Temple, *J. Org. Chem.*, 33(1), 344 (1968), D. D. DesMarteau, *Inorg. Chem.*, 32, 5007 (1993), all of which are incorporated herein by reference in their entirety.

Fluoroalkylenesulfonylfluorides having polymerizable functional groups have been described by Gard et al., J. Fluorine Chem. 66, 105 (1994), Gard et al., Coordination Chemistry Reviews 112, 47 (1992), Gard et al., J. Fluorine Chem., 49, 331 (1990), Gard et al., J. Fluorine Chem. 43, 329 (1989), Gard et al., J. Fluorine Chem. 67, 27 (1994), Gard et al., J. Fluorine Chem. 55, 313 (1991), Gard et al., J. Fluorine Chem. 38, 3 (1988), Gard et al., Inorg. Chem., 29, 4588 (1990), U.S. Pat. No. 5,414,117 (Armand), and U.S. Pat. No. 5,463,005 (DesMarteau). Polymers prepared from fluoroalkylenesulfonylfluorides having polymerizable functional groups have been described in DesMarteau, *Novel Fluorinated Acids for Phosphoric Acid Fuel Cells*, Gas Research Institute Report #GRI-92/0385, July 1992, and J. Fluorine Chem., 72, 203 (1995).

In general, the above-described perfluoro-organic sulfonate salts are prepared as generally described in U.S. Ser. No. 08/398,859 (Waddell et al.) incorporated herein by reference in its entirety. These salts are prepared by hydrolysis of the corresponding perfluoroorganosulfonyl fluoride, via reaction with a basic salt having the desired cation (e.g., a carbonate, hydroxide, or alkoxide salt) in the presence of water and, optionally, an additional polar solvent.

Processes useful for the synthesis of fluorochemical imide salts are described in:

1. D. D. Des Marteau et al., *Inorg. Chem.*, 1984, 23, pp. 3720–3723;
2. D. D. Des Marteau et al., *Inorg. Chem.*, 1990, 29, pp. 2982–2985;
3. Canadian Patent 2000142-A;
4. U.S. Pat. No. 4,505,997; and
5. U.S. Pat. No. 5,072,040.

Processes useful for the synthesis of fluorochemical methide salts and their conjugate acids are described in:

1. U.S. Pat. No. 5,273,840, and
2. Turowsky and Seppelt, *Inorg. Chem.*, (1988) 27 pp. 2135–2137.

To prepare the perfluoroorganosulfonyl fluoride, the corresponding hydrocarbon sulfonyl fluoride (prepared, e.g., according to techniques described in Hansen, U.S. Pat. No. 3,476,753, which is incorporated by reference in its entirety) is perfluorinated by electrochemical fluorination according to the methods described in Hansen U.S. Pat. No. 3,476,753, Simons, U.S. Pat. No. 2,519,983, and *Chemistry of Organic Fluorine Compounds*, Milos Hudlicky, ed., 2d ed., PTR Prentice Hall (New York), pp. 73–76 (all of which are incorporated by reference in their entirety), followed by purification.

In general, the conductivity enhancers of the present invention can be prepared as described in WO95/03338 (Lamanna et al.), incorporated by reference in its entirety, by anion exchange or metathesis reactions by combining salts that contain the desired cation and conventional counteranions, such as chloride, $PF_6^-$, $SbF_6^-$, or $BF_4^-$, with simple salts, such as alkali or alkaline earth metal salts or alkylammonium salts, of the nonnucleophilic anions of the invention in a suitable solvent. Generally, metathesis reactions may be carried out at temperatures ranging from about −80° C. to about 100° C., preferably at ambient temperature, under conditions in which either the salt of the instant invention or the metathesis byproduct(s) selectively precipitates, thus permitting isolation of the salt of the invention in the form of a solution or a pure solid. Alternatively, ion metathesis may be achieved by passing a solution of salt through a column of an insoluble anion exchange resin containing a nonnucleophilic anion of the invention. The salts of the invention will form it situ if the individual components described above are added directly to the composition capable of being applied by electrostatic assistance. It is preferred, however, to form the pure salt conductivity enhancer) in a separate step as a solid or in a suitable solvent prior to adding the same to the electrostatically-assistable composition and performing the coating and polymerization process.

Suitable metathesis solvents generally are capable of dissolving at least one and preferably all of the reagents required for the metathesis reaction without reacting with these reagents. Solvents are generally selected such that the desired salt or the metathesis byproducts selectively precipitate, thus allowing the desired salt to be isolated in relatively pure form. Normally, the preferred solvent for a particular system is determined empirically. In the cases where an anion exchange resin is used, the solvent should not dissolve the resin, but should dissolve the metathesis reagents and the desired product salt. Nonlimiting examples of suitable solvents include water; chlorocarbons, such as methylene chloride, and chloroform; ethers; aromatic hydrocarbons, such as toluene, and chlorobenzene; nitriles, such as acetonitrile; alcohols, such as methanol and ethanol; nitrobenzene; nitromethane; ketones, such as acetone and methyl ethyl ketone; and other similar classes of organic solvents. Mixtures of solvents are often desirable to control solubility of reagents and product salts.

The sodium and lithium salts of $[3,5-(CF_3)_2C_6H_3]_4B^-$ (TFPB$^-$) were prepared following published techniques (H. Kobayashi, et al. in *Bull Chem. Soc., Jpn.*, 57, 2600 (1984) incorporated herein by reference in their entirety.

$[Li[B(C_6F_5)_4]]2(C_2H_5)_2O$ was prepared as described in WO95/03338 (Lamanna et al.) incorporated by reference herein in its entirety.

$C_6F_5Li$ (70 mmole) was prepared according to the method described by A. G. Massey and A. H. Park, Organometallic Synthesis, 3, 461 (1986), modified by using as the solvent a mixture of 200 mL of hexane and 50 mL of diethyl ether. To this mixture at a temperature of −78° C., 17.5 mL of 1.0 M $BCl_3$ in hexane was added dropwise. After stirring overnight, crude product was collected on a Schlenk filter and vacuum dried. The crude material was purified by Soxhlet extraction under vacuum with anhydrous methylene chloride to produce a white, powdery product. This product was dried under high vacuum producing a yield of 13 grams (77 percent). $^1H$ NMR analysis showed the product to contain 2.1 moles of diethyl ether per formula weight. Because the product was hygroscopic, it was stored under dry nitrogen.

Li $[B(n-butyl)(C_6F_5)_3]$ was prepared as described in U.S. Ser. No. 5,514,728 (Lamanna et al.). To a stirred suspension of 1.17 grams (2.3 mmoles) $(C_6F_5)_3B$ in 10 mL of hexane, 0.95 mL of a 2.5 M solution of n-butyllithium in hexane under nitrogen was added. A white solid product precipitated and after 30 minutes it was isolated by filtration and washed with 5 mL hexane. After vacuum drying, the yield was 0.98 gram. $^{11}B$ NMR (toluene): −7.7 (s) ppm relative to $BF_3$ $(OEt_2)$.

The cationic portion of the salts of this invention can be virtually any organic or inorganic cation. For example, preferred cations are alkali metal, alkaline earth metal, or group Va, VIa, or VIIa onium cations such as ammonium, alkylammonium, and other nitrogen-onium, phosphonium, arsonium, iodonium, and sulfonium cations. Said cations may preferably also contain polymerizable functionality for immobilization of the salt.

The most preferred salts can be used at concentrations below 1 weight percent and do not require any dissociation enhancing agent. Dissociation enhancing agent(s) may be added or salts may be used at concentrations greater than 1 weight percent in order to increase the ionic conductivity of relatively nonconductive mixtures.

Conductivity enhancers suitable with cationically polymerizable monomer mixtures, such as epoxies and vinyl ethers, are those that are free of highly nucleophilic anions which tend to combine with the propagating species (the cation of the propagating polymer chain-end) and significantly slow down or inhibit the polymerization. When nucleophilic ions, such as carboxylate, halogenide, and the like are present, polymerization inactive species are readily formed, especially in low dielectric constant media. To avoid this problem, non-nucleophilic anions, such as $BF_4^-$, $PF_6^-$, $AsF_6^-$ and $SbF_6^-$ are commonly employed. With highly nonpolar monomers, such as vinyl ethers and epoxies, it may be beneficial to use slightly more solubilizing anions, such as $CF_3SO_3^-$(triflate), $C(SO_2CF_3)_3^-$, $N(SO_2CF_3)_2^-$, $CH(SO_2CF_3)_2^-$, TFPB$^-$ and the like. With these counterions, polymerizations of cationically curable monomers is still possible. As with the fluorinated inorganic anions (above), the rates of polymerization will vary depending upon the choice of monomer and the degree of non-nucleophilicity of the anion.

Initiators used to cure an electrosprayable mixture of monomers may also be salts and may have the anions of the present invention associated with them to improve their solubility, reactivity, ionic conductivity, and/or stability. Where the ionic catalyst or initiator is sufficiently conductive it may further serve a dual function as both the curing or polymerization initiating agent and as the conductivity enhancer. Mixtures of salts (i.e., initiators and conductivity enhancers) containing the same or different anions may be used in a composition capable of being applied by electrostatic assistance, with the proviso that the mixture is compatible; that is, the salts remain essentially fully dissolved in the monomer mixture and retain their intended activity without interfering with the activity of the other components or initiating polymerization prior to application on the substrate.

Dissociation Enhancing Agents

The dissociation of the ion pairs may also be enhanced by the addition of one or more dissociation enhancing agent(s). These dissociation enhancing agents will associate with (i.e., "stabilize") one or both of the ions of the salt. As with each component, the dissociation enhancing agents when added preferably should meet the "solvent-free" requirements and preferably not interfere with the polymerization. Typically, when dissociation enhancing agent(s) are a part of the composition, at least 0.1 weight percent is added, preferably about 0.5 to about 5 weight percent. Preferred dissociation enhancing agent(s) have a dielectric constant of at least 5 at 20° C. More preferably, the dielectric constant is at least 10 at 20° C., and most preferably is at least 20 at 20° C. Examples are well known in the art and include materials such as polyethylene glycols, crown ethers, and poly (ethylene oxides) which in combination with alkali salts selectively complex the metal ion of the ion pair thus inducing dissociation. Small amounts of co-reactive and more polar monomers such as N-vinylpyrrolidinone can also be used to enhance dissociation, provided they do not adversely affect the properties of the cured coatings.

Monomers

The monomers selected for these compositions are essentially completely miscible with the other components of the mixture. In addition, these monomers have sufficiently low vapor pressures so that little material loss occurs during processing. Preferably, the monomers are non-volatile, or are such that their vapor pressures are 1 kPa or less at 25° C., more preferably 0.5 kPa or less at 25° C., and most preferably 0.1 kPa or less at 25° C. Monomers are also selected and at concentrations based on the desired use for the composition. Useful monomers include both monofunctional and multifunctional monomers.

Typical cationically polymerizable and/or copolymerizable monomers include ethylenically unsaturated compounds, such as vinyl or vinylidene ethers, N-vinyl carbazoles, vinyl silanes, N-vinyl pyrrolidinone, 1,1-dialkyl-, trialkyl-, and tetraalkyl-substituted olefins, cyclic olefins, conjugated diolefins, and styrenes. Other cationically reactive monomers include cyclic ethers, especially strained ones such as epoxides.

Typical useful vinyl ether monomers include vinyloxy groups substituted with alkyl or cycloalkyl groups having between 4 and 18 carbon atoms. Alkyl groups with less than four carbons are generally difficult to handle because of their high volatility and extremely low flash points. Vinyl ethers having more than 18 carbons in the alkyl group are not readily available from commercial sources and are typically sluggish to react.

Vinyl ethers with more than one vinyloxy group are also suitable. They can be combined with the monofunctional materials to enhance the properties by covalently crosslinking the composition.

Examples of these vinyl ethers are n-butyl vinyl ether, isobutyl vinyl ether, 2-ethylhexyl vinyl ether, n-decylvinyl ether, cyclohexyl vinyl ether, cyclohexyl dimethanol divinyl ether, 1,4-butanediol divinyl ether, 1,6-hexanediol divinyl ether, trimethylol propane trivinyl ether and the like.

Electron rich vinyl compounds are also suitable. Also included, though usually less reactive, are substituted vinyl analogs such as isopropenyl ethers and the like. For example, phenyl substituted vinyl compounds and styrenic compounds, such as styrene, α-methyl styrene, anethole, vinyl toluene, t-butyl styrene, vinyl anisole, propenyl phenol, divinyl benzene, and diisopropenyl benzene, can be used. Because these compounds typically polymerize to low molecular weights and hard coatings, they are most commonly copolymerized with other monomers rather than homopolymerized.

Other suitable electron rich olefins include multi-alkyl substituted olefins, di- and polyolefins, and cyclic olefins. Illustrative examples include limonene, pinene, citral, and camphene.

Epoxides are also suitable monomers in these compositions. Because many epoxy monomers are too viscous to be coated by electrostatic assistance, reactive diluents are commonly used with these monomers.

Examples of low viscosity epoxide materials include epoxidized α-olefins sold under the trade name Vikolox™ by Atochem (Philadelphia, Pa.), styrene oxide, limonene oxide, vinyl cyclohexene dioxide (available from Ciba-Geigy (Hawthorne, N.Y.) as Araldite™ RD-4), 1,4-butanediol diglycidylether (available from Ciba-Geigy as Araldite™ RD-2), butyl glycidylether (available from Ciba-Geigy as Araldite™ RD-1), dipentene dioxide (available from Union Carbide, Danbury, Conn., as ERL-4269), and the like.

Other examples, including already diluted materials, can be selected by one skilled in the art from the reference "Handbook of Epoxy Resins," Lee & Neville, McGraw-Hill, 1982, Appendix 4-2, pages 4-58 through 4-70).

Depending on the desired properties of the composition, some cationically coreactive oligomers or polymers may be desirable as part of the composition to modify the performance characteristics.

Examples of these coreactive materials include epoxidized polybutadienes, epoxy functional polydimethylsiloxanes, epoxy functional hydrogenated anionic block copolymers based on isoprene, butadiene and styrene, such as the EKP 201 (epoxidized star polymer) and EKP 207 (linear epoxidized mono-ol polymer) both available from Shell Chemical (Houston, Tex.).

With epoxies, coreactive diluents are commonly used. Examples of these coreactive diluents are vinyl ethers, styrenes, and alcohol functional materials, such as HPVM 1201 or HPVM 1202 both available from Shell Chemical.

Other cationically polymerizable or copolymerizable monomers include strained cyclic amines, such as aziridines and azetidines, cyclic monomers, such as lactams and lactones, five-membered cyclic ethers, trioxane, ketones, and aldehydes. These monomer s are usually less preferred because they may introduce properties, such as water-swellability, which may conflict with the intended use. In certain cases, however, and especially in lesser amounts, they may confer desirably increased adhesion or wettability.

Initiators

Initiators, which may be catalytic, are generally required to activate the polymerization process. The activation energy can be either radiative or thermal. For thermal activation, catalysts can be selected from materials such as Lewis acids, organic protonic acids, or anhydrides. See Radiation Curing in Polymer Science and Technology, Elsevier Applied Science, 1993, vol. 2; Radiation Curing Science and Technology, S. P. Pappas, Plenum Press, N.Y., 1992, incorporated herein by reference. Depending on the reactivity of the monomers, activation temperatures in excess of 100° C. may be required. A common problem with these initiators is the risk of premature polymerization of the monomer/initiator mixtures. In those cases where mixing the monomers with the initiator results in handling difficulties because of premature polymerization, preferably the initiator is applied first on the substrate, followed by deposition of the monomer composition using the selected electrostatic assistance method. If this were necessary, the initiator typically would be essentially nonvolatile at the application temperature, and the very small amounts required preferably may, for example, be applied by conventional vacuum deposition, or from dilute solution.

Blocking of the catalyst is another possibility. Examples could be the use of a volatile base, such as triethylamine, with an organic acid such as $(CF_3SO_2)_2CH_2$. With heat, the acid is freed up and initiation is possible. See, for example, U.S. Pat. No. 4,049,861 (Nozari) and GB 1327205-A (R. Koshar).

Another method of initiating cationic polymerization is to use a catalyst, such as cupric benzoate in combination with the iodonium salts and nucleophilic monomers, which system upon heating "spontaneously" polymerizes. (See Ring Opening Polymerization, J. E. McGrath, ACS Symposium Series, 1985, page 198, incorporated herein by reference). Because the catalyst does not always form a completely soluble mixture as required for electrospray, in those cases the catalyst should first be deposited on the substrate as described above, followed by application of the monomer/initiator mixture.

Ultraviolet light can also be used to initiate polymerization. Useful photoinitiators are completely soluble and stable in the monomer mixture to avoid premature polymerization prior to application on the substrate. If necessary, the initiator can be applied to the substrate first (by any conventional coating method), followed by application of the monomers.

Examples of useful photoinitiators include onium salts selected from, but not limited to, sulfonium salts, iodonium salts and mixtures thereof. Particularly useful are diaryl iodonium salts or sulfonium salts with general structures $Ar_2I^+X^-$ and $Ar_3S^+X^-$, respectively, wherein Ar is an aryl group and $X^-$ is selected from anions of strong monovalent acids such as $BF_4^-$, $PF_6^-$, $AsF_6^-$, $SbF_6^-$, $CF_3SO_3^-$, $ClO_4^-$, and the like. Also useful are organic anions such as $HC^-(SO_2CF_3)_2$, $^-C(SO_2CF_3)_3$, $^-N(SO_2CF_3)_2$, $^-B(C_6F_5)_4$, $C_6H_5C^-(SO_2CF_3)_2$. The less reactive onium salts, having anions such as triflate and perchlorate, are only useful with the more reactive monomers, such as vinyl ethers. The more reactive salts are also useful with slower reacting monomers, such as certain epoxides.

Examples of diaryl iodonium compounds can be found in U.S. Pat. No. 4,279,717 (Eckberg et al.). Triaryl sulfonium salts with general structure $Ar_3S^+X^-$, such as those described in U.S. Pat. Nos. 4,231,511 (Smith et al.), 4,256,828 (Smith et al.), 4,101,513 (Fox et al.), 4,049,861 (Nozari et al.), and 4,058,400 (Crivello et al.) are also suitable.

Examples of onium and organometallic salts of fluorinated aryl borate anions useful as initiators for cationic polymerization can be found in WO95/03338.

Other suitable compounds include ferrocenium salts, such as Irgacure™ 261 from Ciba-Geigy, which are less reactive than the iodonium or sulfonium salts. Depending on the monomers, heating may be required in addition to UV irradiation to complete the cure. (J. Crivello, Radiation Curing in Polymer Science and Technology, Elsevier Applied Science, 1993, Volume II, pages 435–471).

Photosensitizers, such as thioxanthone, anthracene, xanthone, and the like, can be used in combination with these photoinitiators to accelerate the initiation process. See Table 2-1 of the reference Steven L. Murov, Handbook of Photochemistry, Marcel Dekker, Inc., N.Y. 27–35 (1973).

Typically, the initiator concentration is selected based on the reactivity of the monomers and the desired speed of polymerization. For highly reactive monomers, such as vinyl ether compounds, initiator levels will be on the order of about 0.05 to about 1 weight percent. For the less reactive epoxies, initiator levels between about 0.5 and about 4 weight percent are more common.

Some of the initiators, such as the iodonium salts, may have sufficient solubility and ionization in the monomer mixtures to enhance the conductivity sufficiently to allow the deposition by electrostatic assistance. However, the conductivity is dependent on the initiator concentration; and thus, it is basically impossible to change the conductivity without changing the initiator concentration. High initiator concentrations can result in difficult-to-control reaction kinetics or poor aging stability of the polymerized coatings. If the conductivity requirements limit to low levels the initiator concentration that may be used, the polymerization rate can drop below economically acceptable rates.

Therefore, the initiator and the conductivity enhancer concentrations preferably are independently controlled in the electrostatically-assistable compositions of this invention.

Additional Additives

Free-radically polymerizable monomers, such as acrylates, methacrylates, vinyl esters, methacrylamides, acrylamides, fumarates, styrenes, maleimides, and the like, may be added to the cationically polymerizable monomers of the present invention to obtain a "hybrid" composition. When free-radically polymerizable monomers are added, a free-radical initiator must also be added. Free-radical initiators include, but are not limited to, benzoin ethers, camphorquinone, acetophenone derivatives, benzophenone, anthraquinone, benzoylperoxide, 2,2'-azo-bis (isobutyronitrile), 1,1'-azo-bis(cyclohexane-1-carbonitrile), dicumylperoxide, and persulfate/bisulfite redox pairs. Some initiators may trigger both free-radical and cationic polymerization. For example, onium and organometallic salts such as diaryliodonium and triarylsulfonium salts and (cyclopentadienyl)(arene) iron$^+$ salts of the anions $PF_6^-$ and $SbF_6^-$ may be useful.

When two initiators are present, the activation mechanism may be the same or different. When the mechanism is the same (e.g., heat or radiation), initiators can be selected such that the activation energy differential triggers polymerization at different points in time. In some cases, it may be desirable that the cationic and free-radical polymerization occur simultaneously, for example interpenetrating polymer networks useful for coatings. An example of different activation mechanisms is a UV initiator for free-radical polymerization and a heat-activated initiator for cationic polymerization.

In order to achieve specific functionality in the finished coating the monomers and other components are selected to impart the desired properties.

Additives such as flatting agents, dyes, pigments, plasticizers or tackifiers and the like can be used or non-functional flow enhancers and wetting agents can be added to improve the aesthetics of the coating. These additives preferably are soluble in the composition, are nonvolatile, and preferably do not detrimentally interfere with the conductivity or the curability of the compositions.

A composition can be prepared by mixing together in a suitable vessel one or more cationically polymerizable monomer(s) and one or more cationic initiator(s), such that when in combination have a conductivity insufficient to be applied by means of electrostatic assistance (i.e., electrostatically assisted continuous liquid coating, electrostatic spray coating, electrospray coating). One or more conductivity enhancer(s) and optionally one or more dissociation enhancing agent(s) may be added to increase the conductivity yielding an application composition. This application composition may then be applied to a substrate using electrostatic assistance and subsequently polymerized. Typically, the substrate has two major surfaces, and the composition is applied to at least a portion of at least one major surface.

One embodiment of the present invention is a release coating composition on a substrate where the substrate comprises a backing having first and second sides, an adhesive layer having two sides, one side coated onto the first side of the backing, and a release layer on the second side of the backing comprising the polymerized composition formulated as a release coating. Preferably the release coating composition is electrosprayed onto the second side of the backing. When the release coating is used on pavement marking tapes and other such rolled substrates, the substrate is rolled such that the first side of the backing (if already adhesive coated, the adhesive layer) contacts the release layer.

Other embodiments include, but are not limited to, primers, thin adhesives, anti-fogging coatings, ice release coatings, anti-graffiti coatings, abrasion resistant coatings, durable coatings, light-scattering coatings, hard coats, stain resistant coatings, scuff-resistant coatings, and matte surface coatings. Suitable monomers and additives for each application as well as choice of coating thickness may be readily selected by those skilled in the art.

Suitable substrates include, but are not limited to, a sheet, a fiber, or a shaped object provided the substrate does not contain sufficient basic groups which can locally deactivate the initiation or propagation process. The composition may be applied to at least one major surface of suitable flexible or inflexible backing materials and then cured. Useful flexible backing materials include plastic films such as poly (propylene), poly(ethylene), poly(vinyl chloride), poly (tetrafluoroethylene), polyester (e.g., poly(ethylene terephthalate)), polyimide film such as DuPont's Kapton™, cellulose acetate, and ethyl cellulose. Backings may also be constructions with irregular surfaces such as woven fabric, nonwoven fabric, paper, or rough surfaces. Backings can thus also be of woven fabric formed of threads of synthetic or natural materials such as cotton, nylon, rayon, glass, or ceramic material, or they can be of nonwoven fabric such as air-laid webs of natural or synthetic fibers or blends of these, provided they are not too porous. Due to its high porosity, paper itself is usually not suitable unless heavier coatings of greater than one micrometer are applied to offset soaking into the paper. However, glassine, plastic coated, or impregnated paper is suitable. Rough surfaces include embossed or patterned surfaces or particle impregnated resins such as abrasive particle covered (epoxy) resin and glass bead covered resins provided the surfaces, resins, or particles are not so basic in nature as to interfere with polymerization. In addition, suitable substrates can be formed of metal, metallized polymeric film, ceramic sheet material, natural or synthetic rubber, or pavement marking tapes.

EXAMPLES

The following examples illustrate various specific features, advantages, and other details of the invention. The particular materials and amounts recited in these examples, as well as other conditions and details, should not be construed in a manner that would unduly limit the scope of this invention.

Solubility Test

The solubility of the conductivity enhancer for each composition was determined by the following method. A sample of the conductivity enhancer was mixed with a clear monomer solution at room temperature for a maximum of two hours and then checked under agitation for optical clarity. If the conductivity enhancer containing sample was not totally clear or a "true solution", the sample was moderately heated (such that the sample could be held by hand) and then allowed to cool to room temperature. A sample which contained visible conductivity enhancer particles was deemed to have failed.

Viscosity Measurement

The Brookfield viscosity (in centipoise (cp), 1 cp=1 mPa·s) was measured at room temperature with a Brookfield digital viscometer model DV-II available from Brookfield Engineering Laboratories, Inc., Stoughton, Mass.

Conductivity Measurements

The electrical conductivity of a solution was measured by inserting a simple cell composed of two parallel stainless steel rods acting as electrodes into a glass jar containing the solution. The rods, each about 9 cm long and about 3 mm in diameter, were separated by 1 cm center-to-center spacing and were maintained parallel by having both rods embedded at one end into a piece of insulated material (either a standard rubber bottle stopper or a piece of Garolite available from McMaster-Carr, Chicago, Ill.). The height H was the height of the solution meniscus relative to the bottom of the rod. When the rods were placed in a solution at height H, and an electrical potential was applied across the rods, an electrical current attempted to flow between the rods. The solution, air, and insulator provided a net resistance R to the electrical current flow. When the rods were placed to height H in a solution that was reasonably more conductive than air, then the effective resistance was that of the solution. For example, the conductivity of air is approximately $10^{-12}$ S/m or $10^{-6}$ $\mu$S/m, and the conductivity of insulators is even lower, thus for a solution having a conductivity greater than 0.001 $\mu$S/m the resistance R, to within 0.1 percent, was effectively due only to the solution. Resistance R is directly proportional to a geometry factor G and is inversely proportional to the electrical conductivity $\sigma$, and thus G=R$\sigma$. G depends on the height H as well as other fixed parameters such as the separation-distance of the rods and the diameter of the rods. If these fixed parameters are defined as a second geometry factor g then, g=GH where g is a constant defined by the specific geometry of the electrode structure. The value of g was determined using a solution having a known conductivity $\sigma_0$ which gives a resistance $R_0$ when the rods are placed to some specific height $H_o$ in the solution. Because $\sigma_0$ was known and $R_0$ was measured, the geometry factor $G_0$ was determined from $G_0=R_0\sigma_0$. Knowing $H_0$, g was determined using g=$G_0H_0$. Because g is a constant, g=$G_0H_0$=GH, and because g is known, G can be determined for any rod-electrode immersion depth H.

To calibrate the rod-electrode cell, the cell constant g was determined using several salt solutions of known conductivity (Standard Reference Materials (1500, 10000 and 50000 $\mu$S/m), available from National Institute of Standards and Technology (NIST), Gaithersburg, Md.). The constant g varied from about 60 cm/m at 1500 $\mu$S/m to a value of about 70 cm/m at 50,000 $\mu$m. When an impedance analyzer was used to measure the dielectric constant of methanol, isopropyl alcohol (IPA) and methyl ethyl ketone (MEK), g had to be adjusted to obtain the dielectric constant values noted in the Handbook of Chemistry and Physics (CRC Press, Inc., Boca Raton, Fla.). When these g values were plotted against the natural logarithm of the measured conductivity for IPA, MEK, and methanol, and the g values determined using the NIST solutions were also plotted against the natural logarithm of the NIST solution values, all g values fell on the same straight line. As a result, g=59.45 cm/m was chosen which gave the exact conductivity at 1000 $\mu$S/m. With this value of g, all reported conductivity data deviated by about 10 percent per conductivity decade away from 1000 $\mu$S/m, being lower for conductivity below 1000 $\mu$S/m and higher for conductivity above 1000 $\mu$S/m. For example, a conductivity reported as 100 $\mu$S/m was actually about 10 percent lower, one reported as 10 $\mu$S/m is actually about 20 percent lower, etc. Using g=59.45 cm/m, the conductivity $\sigma$ was determined from the resistance across the cell by the formula $\sigma$=g/(HR), where R is the resistance of the solution when the cell was inserted in the solution to height H.

Three methods were used to determine the resistance R and hence the conductivity $\sigma$ of the solution.

In Method I, a Hewlett Packard LF (Low Frequency) Impedance Analyzer Model 4192A (Hewlett Packard Company, Palo Alto, Calif.) was connected across the cell and the admittance Y and the angle D was recorded at frequencies F of 100, 300, 500, 700, 900, and 1000 kilohertz (kHz) along with the immersion depth H of the rods in the solution. This information was used to calculate the conductivity by the formula $\sigma$=(gY cos D)/H. For Method I, the dielectric constant $\epsilon_r$ of the solution may also be computed by the formula $\epsilon_r$=(gY sin D)/(2$\pi\epsilon_0$FH) where $\epsilon_0$ is the permittivity of free space (8.85×$10^{-12}$ farads per meter (F/m)).

In Method II, a BK Precision Model 878 Universal LCR Meter (BK Precision, Maxtec International Corporation, Chicago, Ill.) was connected across the cell and the resistance R at a frequency F of 1 kHz was measured along with the immersion depth H of the rods in the solution. The conductivity was then computed by the formula $\sigma$=g/(HR).

In Method III, the cell was connected in series with a resistor $R_s$ of 1 M$\Omega$, a micro-ammeter A and a switch S. This series circuit was then connected across a standard 9-volt dry cell battery. After the cell was immersed to a height H in the solution the switch S was momentarily closed and the initial reading $I_s$ on the ammeter was recorded. Along with $I_s$, the immersion depth H of the electrodes was recorded. In Method III, the battery voltage $V_b$ may be connected across a switch placed in series with the ammeter and a calibration resistor $R_c$ of 1 MΩ. When this switch was closed the measured current $I_c$ times the resistance $R_c$ gave the voltage of the battery. This information was then used to calculate the conductivity of the solution by the formula $$\sigma = \frac{g}{\left(H\left[\frac{IcRc}{Is}\right] - Rs\right)}$$

electrosprayable solution, after the addition of 3.5 pph of the HQ-115. When exposed to UV light (300 W/inch (11.8 kW/m) Fusion H-bulb, 1 pass at 100 fpm (30.5 m/min)), the mixture polymerizes to form a release coating upon exiting the curing unit.

One limitation with this mixture is the shelf-life of the solution. Even when stored in the dark, the viscosity of the solution slowly increased. Therefore, when using HQ-115, it is recommended that only small batches be mixed or that the photoinitiator be separately delivered (for example, co-sprayed or placed on the web prior to application of the composition) or metered into the solution immediately prior to coating.

Table of Components

| Component | Source |
|---|---|
| 2-Et-4-Me-imidazole.HTFPB 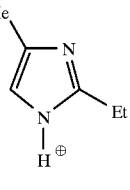 | generally described in WO95/03338 (Lamanna et al.) |
| Araldite RD-1 ™ (a low viscosity epoxy resin) | Ciba-Geigy Corp., Ardsley, NY |
| Bu$_4$N C(SO$_2$CF$_3$)$_3$ | generally WO95/03338 (Lamanna et al.) |
| CHVE (1,4-cyclohexyl dimethanol divinylether) | GAF ISP Technologies, Wayne, NJ |
| DDSA (dodecenyl succinic anhydride) | Anhydrides and Chemicals, Inc., Newark, NJ |
| DDVE (dodecylvinylether) | GAF ISP Technologies, Wayne, NJ |
| DVE-3 (3,6,9,12-tetraoxatetradeca-1,13-diene) | GAF ISP Technologies, Wayne, NJ |
| GE 9380C | GE Silicones, Waterford, NY |
| HQ-115 Fluorad brand lithium (bis)trifluoromethanesulfonamide | 3M Company, St. Paul, MN |
| limonene (olefin) | Aldrich Chemical Co., Milwaukee, WI |
| lithium 4-pentafluoroethyl-perfluorocyclohexane sulfonate | FC98, 3M Co., St. Paul, MN (potassium salt) convert to Li salt by ion exchange |
| Me$_4$NC(SO$_2$CF$_3$)$_3$ | generally, U.S.S.N. 08/558,245 (Lamanna et al.) |
| NaBF$_4$ | Aldrich Chemical Co., Milwaukee, WI |
| NaTFPB 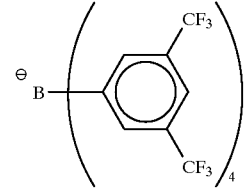 | described in WO95/03338 (Lamanna et al.) |
| NH$_4$BF$_4$ | Aldrich Chemical Co., Milwaukee, WI |
| UV9300 epoxy-silicone | GE Silicones, Waterford, NY |

Example 1

A cationically curable monomer mixture was prepared by mixing at room temperature 25 g UV9300 epoxy-silicone, 75 g limonene, and 3 g of GE 9380C UV initiator. The resistance of the mixture at height H=4 cm was in excess of the 10 MΩ instrument limitation as measured using Method II. The addition of 0.5 pph HQ-115 decreased the resistance to 8.2 MΩ (1.8 μS/m conductivity). Then an additional 0.5 pph HQ-115 was added to the mixture further decreasing the resistance to 5.5 MΩ (2.7 μS/m conductivity). An additional amount of HQ-115 was added to the mixture, to bring the total amount added to 3.5 pph. The resistance further decreased to about 893 kΩ (16.6 μS/m conductivity). This mixture's conductivity is in the most preferred range for an

Example 2

The same monomer mixture was prepared as described in Example 1 (prior to the addition of HQ-115). The addition of 0.5 pph NaTFPB to the epoxysilicone/limonene mixture decreased the resistance to 439 kΩ (34 μS/m conductivity) using Method II. The addition of 3 pph GE 9380C initiator further reduced the resistance to 141 kΩ (105 μS/m conductivity). This sample did not increase in viscosity overnight and polymerized when exposed to UV light to form a release coating.

Example 3

The composition described in Example 2 was prepared substituting 0.2 pph NaTFPB for 0.5 pph. This composition had a conductivity of 28 $\mu$S/m as measured according to Method I. The composition was electrosprayed from a single, number 24 stainless steel biomedical pipetting needle, 1.25 mm ID, 2.15 mm OD (obtained from Popper & Sons, Inc., New Hyde Park, N.Y.). This needle was inserted through the center of 19.1 mm diameter hole in a metal plate such that its fluid exit end protruded 8 mm below a metal plate. The metal plate was held at ground potential as was a second grounded metal plate located 11 cm below the tip of the needle. The sample was placed in a suitable container (covered glass jar) and drawn out by a pump (Masterflex™ 100 RPM pump drive Model 7530-35, Micropump™ Model 07002-25 pump head both available from Cole-Parmer Instrument Co., Chicago, Ill.) and moved along a 5.2 m length of semiflexible nylon 6/6 tubing 2.44 mm ID, 3.18 mm OD, 0.38 mm wall (and suitable fittings all obtained from McMaster-Carr Supply Co., Elmhurst, Ill.) to the needle. A high voltage was applied between the needle and the ground plate using a negative power supply (Model PS/WG-20N15-DM, available from Glassman High Voltage, Inc., Whitehouse Station, N.J.). At a flow rate of 136 microliters per minute (8160 microliters per hour) and at a potential of −4 kV, a stable electrospray was obtained as observed by a stable cone and filament at the tip of the needle. Both the conductivity and flow rate were consistent with those in a typical electrospray process (e.g., U.S. Pat. No. 4,748,043, Example 2).

Example 4

A sample was prepared by mixing at room temperature 20 g DDVE, 12 g DVE-3, and 0.44 g HQ-115. Using Method II the resistance was 469 k$\Omega$ (32 $\mu$S/m conductivity), whereas without the HQ-115, the resistance was in excess of 10 M$\Omega$, the limitation of the instrument.

The addition of 0.64 g GE 9380C initiator decreased the resistance to 121 k$\Omega$ (123 $\mu$S/m conductivity). The sample was then coated on a polyester liner and polymerized with one pass at 75 fpm (22.9 m/min) under a 300 W/in (11.8 kW/m) Fusion H-bulb.

Example 5

This example was prepared as described in Example 4, substituting DDSA (a thermal initiator for cationic polymerization) for the GE 9380C UV initiator. Using Method II, the resistance was 251 k$\Omega$ (59 $\mu$S/m conductivity). This sample can be heat-cured.

Example 6

These samples demonstrate the effectiveness of different salts in cationically curable monomers, such as an epoxy (Araldite RD-1), an olefin (limonene), and a vinyl ether (CHVE). The samples demonstrate that the salts of the present invention can be used to change the conductivity of the monomers. Limonene, which is less polar than the Araldite RD-1, is a less favorable environment for salts to dissociate as indicated by the lower conductivity values at similar salt concentrations. The more polar and already conductive Araldite can be more readily modified.

The salts preferably have minimal protonic or Lewis acidity, otherwise they can prematurely polymerize the more reactive monomers, for example, such as HQ-115 in combination with CHVE. The sample's current was measured in microamperes ($\mu$A) using Method III.

| Sample | Conductivity Enhancer | Concentration (pph) | Monomer | Soluble | Current ($\mu$A) at H = 5 cm | Conductivity ($\mu$S/M) |
|---|---|---|---|---|---|---|
| 1 | none | | Araldite RD-1 | | 6.4 | 26.4 |
| 2 | NaTFPB | 0.05 | Araldite RD-1 | yes | 8.7 | 180 |
| 3 | 2-Et-4-Me-imidazole-H TFPB | 0.05 | Araldite RD-1 | yes | 8.7 | 180 |
| 4 | Bu$_4$N C(SO$_2$CF$_3$)$_3$ | 0.05 | Araldite RD-1 | yes | 8.4 | 114 |
| 5 | NaBF$_4$ | 0.05 | Araldite RD-1 | yes | 8.4 | 114 |
| 6 | NH$_4$BF$_4$ | 0.05 | Araldite RD-1 | partially | 7.9 | 68.3 |
| 7 | Me$_4$NC(SO$_2$CF$_3$)$_3$ | 0.05 | Araldite RD-1 | yes | 8.7 | 180 |
| 8 | lithium 4-pentafluoroethyl-perfluorocyclohexane sulfonate | 0.05 | Araldite RD-1 | yes | 8.7 | 180 |
| 9 | none | | Limonene | | 0.0 | N/A |
| 10 | 2-Et-4-Me-imidazole-H TFPB | 0.05 | Limonene | yes | 0.4 | 0.53 |

-continued

| Sample | Conductivity Enhancer | Concentration (pph) | Monomer | Soluble | Current ($\mu$A) at H = 5 cm | Conductivity ($\mu$S/M) |
|---|---|---|---|---|---|---|
| 11 | NaTFPB | 0.05 | Limonene | yes | 0.7 | 0.97 |

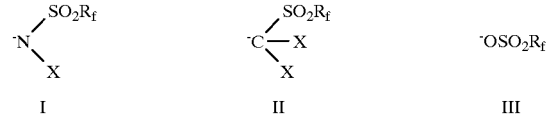

| 12 | Bu$_4$N C(SO$_2$CF$_3$)$_3$ | 0.05 | Limonene | very low | 0.0 | N/A |
| 13 | none | | CHVE | | 0.0 | N/A |
| 14 | 2-Et-4-Me-imidazole-H TFPB | 0.05 | CHVE | yes | 1 | 1.43 |
| 15 | NaTFPB | 0.05 | CHVE | yes | 3 | 5.67 |
| 16 | HQ-115 (LiN(SO$_2$CF$_3$)$_2$ | 0.02 | CHVE | yes | unstable | N/A |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A cationically polymerizable composition suitable for application to a substrate by means of electrostatic assistance and comprising:
   a) one or more cationically polymerizable monomer(s);
   b) one or more cationic initiator(s); and
   c) one or more non-volatile conductivity enhancer(s) having cationic and anionic portions, which are soluble in said monomer(s) and which do not interfere with polymerization, wherein the anionic portion is a noncoordinating organophilic carbon-containing anions, and wherein said conductivity enhancer(s) is a chemically different component than said initiator(s);
   said composition having a conductivity sufficient to be applied to a substrate by means of electrostatic assistance and said monomer(s) and initiator(s) being such that when in combination they have a conductivity insufficient to be applied to a substrate by means of electrostatic assistance.

2. The composition according to claim 1 wherein said composition is solvent-free.

3. The composition according to claim 1 wherein said monomer(s) is selected from the group consisting of vinyl ethers, vinylidene ethers, N-vinyl carbazoles, vinyl silanes, N-vinyl pyrrolidinone, 1,1-dialkyl, trialkyl-, and tetraalkyl-substituted olefins, styrene and substituted styrenes, cyclic and acyclic olefins, conjugated diolefins, epoxides, cyclic ethers, and mixtures thereof.

4. The composition according to claim 1 wherein said initiator(s) is selected from the group consisting of Lewis acids, organic protonic acids, anhydrides, onium salts, ferrocenium salts, and salts of organometallic cations.

5. The composition according to claim 1 wherein said initiator ranges from about 0.05 percent by weight to about 4 percent by weight based on the total weight of said composition.

6. The composition according to claim 1 wherein said noncoordinating organophilic carbon-containing anion has a formula weight of at least 200 kg/kmol.

7. The composition according to claim 1 wherein said conductivity enhancer concentration ranges from about 0.001 percent by weight to about 10 percent by weight based on the total weight of said composition.

8. The composition according to claim 1 wherein said noncoordinating organophilic carbon-containing anion is selected from the group consisting of alkyl-, cycloalkyl- and arylsulfonates, fluoroalkylsulfonylimides, fluoroalkylsulfonylmethides, arylborates, carborane anions, metallocarborane anions, and boron catecholates.

9. The composition according to claim 1 wherein said noncoordinating organophilic carbon-containing anion is fluorinated.

10. The composition according to claim 1 wherein said noncoordinating organophilic carbon-containing anion has one of the following formulae:

$$\begin{array}{ccc} \text{N}\!\!\diagup\!\!\!\!^{SO_2R_f}_{\diagdown X} & \text{C}\!\!\diagup\!\!\!\!^{SO_2R_f}_{\diagdown X}\!\!-\!\!X & {}^-OSO_2R_f \\ I & II & III \end{array}$$

wherein:

X is selected from the groups: H, alkyl, alkenyl, aryl, alkaryl, —SO$_2$R, —SO$_2$R$_f$, —C(O)R, SO$_2$F, and —C(O)R$_f$;

R is selected from the groups: alkyl, cycloalkyl, aralkyl, substituted alkyl, aryl, and substituted aryl; and R$_f$ is a monovalent fluorinated saturated aliphatic radical containing at least one carbon atom.

11. The composition according to claim 10 wherein R$_f$ is a perfluoroalkyl or perfluorocycloalkyl group.

12. The composition according to claim 10 wherein X is a —SO$_2$R$_f$ group and R$_f$ is a perfluoroalkyl or perfluorocycloalkyl group.

13. The composition according to claim 10 wherein said noncoordinating carbon-containing anion is an imide or methide anion of formula (I) or formula (II).

14. The composition according to claim 1 wherein said noncoordinating organophilic carbon-containing anion has the formula:

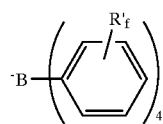

wherein R'$_f$ is one or more fluorinated substituent(s) per aromatic ring and is selected from the group consisting of one or more fluorine atoms or monovalent fluorinated saturated aliphatic radicals containing at least one carbon atom.

15. The composition according to claim 14 wherein the total number of non-ring carbon atoms in the fluorinated substituent(s) R'$_f$ is collectively no greater than 4 per aromatic ring.

16. The composition according to claim 14 wherein said noncoordinating organophilic carbon-containing anion is chosen from the group consisting of tetrakis[pentafluorophenyl]borate and tetrakis[3,5-bis-trifluoromethylphenyl]borate.

17. The composition according to claim 1 wherein the cationic portion of the conductivity enhancer is selected from the group consisting of alkali or alkaline earth metal cations or group Va, VIa, or VIIa onium ions.

18. The composition according to claim 1 further comprising at least 0.1 percent by weight of one or more dissociation enhancing agent(s).

19. The composition according to claim 18 wherein said dissociation enhancing agent(s) are selected from the group consisting of crown ethers, polyethylene glycols, poly(ethyleneoxides), and N-vinylpyrrolidinone.

20. The composition according to claim 18 wherein said dissociation enhancing agent(s) have a dielectric constant of at least 5 at 20° C.

21. The composition according to claim 1 wherein viscosity measures from about $10^{-3}$ Pa·s to about 10 Pa·s.

22. The composition according to claim 1 wherein viscosity measures from about $10^{-3}$ Pa·s to about 2 Pa·s.

23. The composition according to claim 1 wherein viscosity measured from about $10^{-3}$ Pa·s to about 1 Pa·s.

24. The composition according to claim 1 wherein conductivity is from about $10^{-7}$ S/M to about $10^{-1}$ S/m.

25. The composition according to claim 1 wherein conductivity ranges from about $10^{-5}$ S/m to about $10^{-4}$ S/m.

26. The composition according to claim 1 wherein conductivity ranges from about $10^{-5}$ S/m to about $10^{-4}$ S/M.

27. The composition according to claim 1 wherein said composition has a viscosity and a conductivity suitable for application to a substrate by electrospray.

28. The composition according to claim 1 wherein said composition has a viscosity and a conductivity suitable for application to a substrate by electrostatic spray.

29. The composition according to claim 1 wherein said composition has a viscosity and a conductivity suitable for application to a substrate by electrostatically assisted continuous liquid coating.

30. The composition according to claim 29 wherein said continuous liquid coating is selected from roll, curtain, slot, slide, and gravure.

31. The composition according to claim 1 wherein said composition is a primer, a thin adhesive, an anti-fogging coating, an ice release coating, an anti-graffiti coating, an abrasion-resistant coating, a durable coating, a light-scattering coating, a stain-resistant coating, scuff-resistant coating, or a matte surface coating.

* * * * *

UNITED STATES PATENT AND TRADEMARK OFFICE
CERTIFICATE OF CORRECTION

PATENT NO. : 5,962,546
DATED : October 5, 1999
INVENTOR(S) : Albert I. Everaerts, William M. Lamanna, Albert E. Seaver, and George V.D. Tiers It is certified that error appears in the above-identified patent and that said Letters Patent is hereby corrected as shown below:

Column 10,
Line 4, "$SO_3CF_3$," should read -- $SO_2CF_3$, --;
Line 8, "$(SO_3CF_3)_2$," should read -- $(SO_2CF_3)_2$, --;
Line 15, Line 63, "$C_{65})_3FB^{--}$," should read -- $C_6F_5)_3FB^{--}$, --;

Column 12,
Line 49 "it situ" should read -- *it situ* --;
Line 53, "conductivity" should read -- (conductivity --;

Column 13,
Line 32, "Ser. No. 5,514,728" should read -- Pat. No. 5,514,728 --; and Column 20,
Line 52, "of0.5" should read -- of 0.5 --.

Signed and Sealed this

Twenty-fifth Day of December, 2001

Attest:

*Attesting Officer*

JAMES E. ROGAN
*Director of the United States Patent and Trademark Office*